(12) United States Patent
Colvin, Jr. et al.

(10) Patent No.: US 7,375,347 B2
(45) Date of Patent: May 20, 2008

(54) SYSTEMS AND METHODS FOR EXTENDING THE USEFUL LIFE OF OPTICAL SENSORS

(75) Inventors: Arthur Earl Colvin, Jr., Mt. Airy, MD (US); Jeffery C. Lesho, Brookeville, MD (US); Carrie R. Lorenz, Woodbine, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 225 days.

(21) Appl. No.: 10/831,346

(22) Filed: Apr. 26, 2004

(65) Prior Publication Data

US 2005/0236580 A1    Oct. 27, 2005

(51) Int. Cl.
*G01N 21/64* (2006.01)
(52) U.S. Cl. .................... 250/459.1; 250/252.1
(58) Field of Classification Search ............ 250/459.1, 250/252.1
See application file for complete search history.

(56) References Cited

U.S. PATENT DOCUMENTS

| | | | |
|---|---|---|---|
| 5,342,408 A * | 8/1994 | deCoriolis et al. ............ 607/32 |
| 5,512,246 A | 4/1996 | Russell et al. | |
| 5,517,313 A | 5/1996 | Colvin, Jr. | |
| 5,833,603 A | 11/1998 | Kovacs et al. | |
| 6,256,522 B1 | 7/2001 | Schultz | |
| 6,330,464 B1 | 12/2001 | Colvin, Jr. et al. | |
| 6,574,425 B1 | 6/2003 | Weiss et al. | |
| 2002/0026108 A1 | 2/2002 | Colvin, Jr. | |
| 2002/0043651 A1 | 4/2002 | Darrow et al. | |
| 2002/0151772 A1 | 10/2002 | Polak | |
| 2004/0197267 A1* | 10/2004 | Black et al. ................. 424/9.6 |

FOREIGN PATENT DOCUMENTS

| WO | WO 00/64492 A1 | 11/2000 |
|---|---|---|
| WO | WO 02/078352 A1 | 10/2002 |

* cited by examiner

*Primary Examiner*—David P. Porta
*Assistant Examiner*—Djura Malevic
(74) *Attorney, Agent, or Firm*—Rothwell, Figg, Ernst & Manbeck

(57) ABSTRACT

The present invention provides a method for increasing the lifetime of an optical sensor. In one aspect, the method includes the step of configuring the optical sensor so that the duty cycle of sensor's radiant source is less than 100% over a continuous period amount of time when the sensor is periodically obtaining data regarding an analyte. By operating the sensor according to the above inventive method, the indicator molecules of the optical sensor are not excited during the entire continuous period of time during which the sensor is needed to provide data regarding the presence or concentration of a substance. Thus, the method increases the life of the indicator molecules.

58 Claims, 16 Drawing Sheets

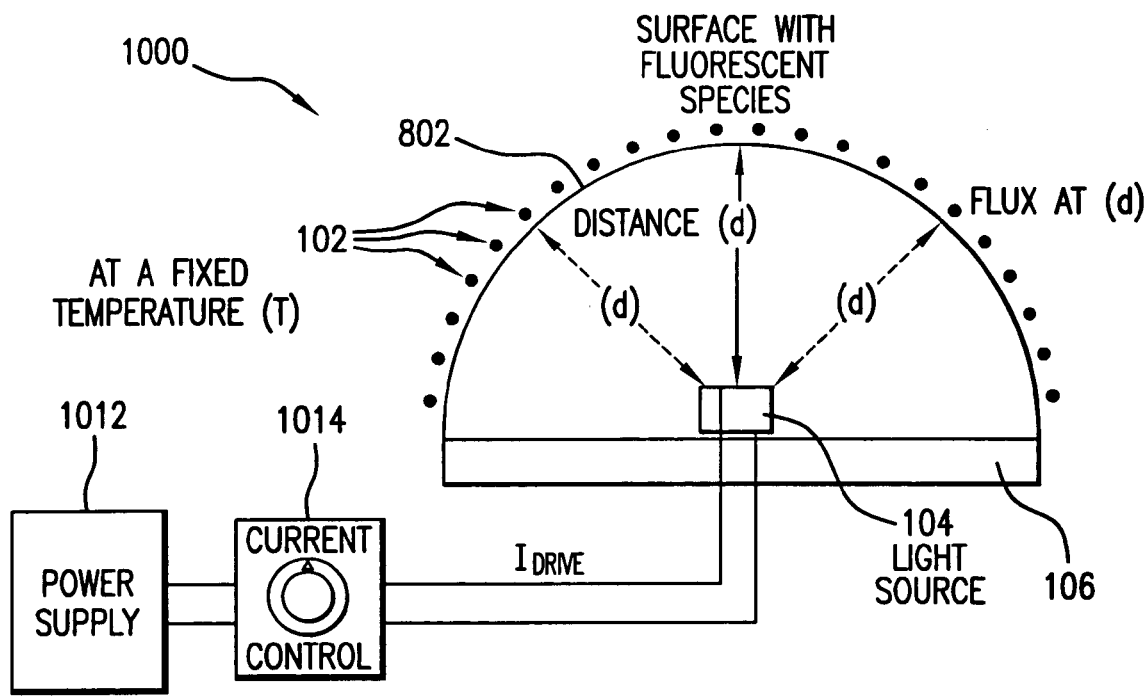

- CURRENT FLOW SETS SOURCE INTENSITY

- SOURCE INTENSITY SETS FLUX DENSITY THROUGH DISTANCE (d) AND THE INVERSE SQUARE LAW

- FLUX DENSITY IS DIRECTLY PROPORTIONAL TO THE RATE OF PHOTO-OXIDATION

- ∴ THEREFORE, THE REGULATION OF CURRENT FROM THE POWER SUPPLY TO THE LUMINOUS SOURCE, SETS THE SOURCE INTENSITY, WHICH THROUGH A FIXED DISTANCE (d), GOVERNED BY THE INVERSE SQUARE LAW, ESTABLISHES THE FLUX, WHICH SETS THE RATE OF PHOTO-OXIDATION AND THUS THE RATE OF SIGNAL DEGRADATION.

FIG.10

SYSTEMS AND METHODS FOR EXTENDING THE USEFUL LIFE OF OPTICAL SENSORS

BACKGROUND OF THE INVENTION

1. Field of the Invention

The present invention relates to sensors that detect the presence or concentration of a particular substance using a radiant source, a photodetector and indicator molecules, which have an optical characteristic that is affected by the presence of the substance. Such sensors are referred to herein as "optical sensors." In one aspect, the present invention relates to systems and methods for extending the useful life of optical sensors.

2. Discussion of the Background

U.S. Pat. No. 5,517,313, the disclosure of which is incorporated herein by reference, describes a sensing device comprising a radiant source (e.g., a light-emitting diode—"LED"), fluorescent indicator molecules, and a photoelectric transducer (e.g., a photodiode, phototransistor, photomultiplier, or other photodetector). The sensing device may also include a high-pass or bandpass filter. Broadly speaking, in the context of the field of the present invention, an indicator molecule is a molecule having one or more optical characteristics that are affected by the local presence of a particular substance. U.S. Pat. No. 6,330,464, the disclosure of which is incorporated herein by reference, also describes an optical-based sensing device.

In the device according to U.S. Pat. No. 5,517,313, the radiant source (a.k.a., the "light" source) is positioned such that radiation (e.g., visible light or other wavelengths of electromagnetic waves) emitted by the radiant source strikes the fluorescent indicator molecules, thereby causing the indicator molecules to fluoresce. The high-pass filter is configured to allow the radiation emitted by the indicator molecules to reach the photoelectric transducer while filtering out scattered radiation from the light source.

The fluorescence of the indicator molecules employed in the device is modulated (i.e., attenuated or enhanced) by the local presence of a particular substance. For example, the orange-red fluorescence of the complex tris(4,7-diphenyl-1,10-phenanthroline)ruthenium(II) perchlorate is attenuated by the local presence of oxygen. Therefore, this complex can be used as the indicator molecule in an oxygen sensor. Indicator molecules whose fluorescence properties are affected by various other substances are known as well. Furthermore, indicator molecules which absorb light, with the level of absorption being affected by the presence or concentration of a particular substance, are also known. For example, U.S. Pat. No. 5,512,246, the disclosure of which is incorporated by reference, discloses compositions whose spectral responses are attenuated by the local presence of polyhydroxyl compounds such as sugars.

Advantageously, the photoelectric transducer element of the device is configured to output a signal that is a known function of the amount of light incident thereon. Thus, because the high-pass filter allows only the light from the indicator molecules to reach the photosensitive element, the photoelectric transducer outputs a signal that is a function of the amount of light coming from the indicator molecules. And because the amount of light coming from the indicator molecules is a function of the concentration of the local substance, the signal outputted by the photoelectric transducer can be calibrated to be indicative of the concentration of the local substance. In this manner, one can detect the presence or concentration of a particular substance.

One particular challenge in commercializing such optical sensors as the one described above is to provide for a useful period of shelf and/or operational lifetime. The standard electronic components commonly used in such sensors have useful lifetimes typically exceeding 10 years or more, which is adequate for most commercial products. However, the chemical components of these hybrid sensors (e.g., the indicator molecules) must also support extended lifetime product stability in order to meet the practical criteria of commercial utility.

Unfortunately, light catalyzed oxidation (also termed photo-oxidation or photobleaching) is a common photochemical reaction that occurs with many indicator molecules. In this reaction, when an indicator molecule is excited by a particular incident wavelength of electromagnetic energy, an electron is elevated to an excited energy state. While in the excited state, the molecule can (and does) undergo a reaction with ambient oxygen that results in an irreversible addition of oxygen to the molecular structure of the molecule. The oxidized product species is typically no longer fluorescent, and therefore no longer useful.

When the molecule is in this "non-functioning" state, the molecule is said to be photobleached. A typical half life for this photobleaching reaction is on the order of hours. An example of an indicator molecule that becomes photobleached within hours is anthracene (the photo-oxidized product, anthraquinone, is not fluorescent).

A sensor that utilizes fluorescent indicator molecules as a component to recognize and convert the presence of a substance into a measurable signal is limited in its useful life by the degradation and ultimate loss of signal caused by photobleaching (or photo-oxidation). The microelectronic components of an optical sensor may have useful lifetimes exceeding 10 years, whereas the half-life of the important indicator chemistry component may last only hours or days. This incompatibility in component operational lifetime ultimately limits a product to the shorter useful life of the indicator chemistry.

Therefore, a need exists to compensate for these extreme mismatches in component lifetime to permit commercialization of such products.

SUMMARY OF THE INVENTION

The present invention provides systems and methods that overcome the above mentioned and other disadvantages of the existing art.

In one aspect, the present invention provides a method for increasing the useful lifetime of an optical sensor that, when activated, is configured to obtain data regarding the presence or concentration of a substance within a certain area at least once every X amount of time (e.g., seconds, minutes, hours) for a continuous period of time. The method includes the steps of: (a) configuring the optical sensor so that the duty cycle of the radiant source is greater than 0% but less than 100% during the period of time when the optical sensor is active; (b) positioning the optical sensor at a location within the area; (c) activating the optical sensor for a period of Z amount of time after performing step (b), wherein Z is greater than 0; (d) operating the radiant source so that the duty cycle of the radiant source is greater than 0% but less than 100% during the Z amount of time when the optical sensor is active; and (e) de-activating the optical sensor after the Z amount of time has elapsed.

By operating the sensor according to the above inventive method, the indicator molecules of the optical sensor are not illuminated for the entire continuous period of time during which the sensor is active. Thus, the method increases the useful life of the indicator molecules and, thereby, increases the useful product life of the optical sensor.

In another embodiment of the invention, the method for increasing the useful lifetime of an optical sensor that provides data regarding the presence or concentration of a substance within an area, wherein the optical sensor includes (i) indicator molecules having an optical characteristic that is affected by the presence of the substance, (ii) a radiant source and (iii) a photodetector, includes the steps of: (a) positioning the sensor in a location in the area; (b) activating the sensor, thereby placing the sensor in an active state; (c) after performing step (b), configuring the radiant source so that the radiant source outputs electromagnetic waves having a frequency within a certain frequency range and having an amplitude within a certain amplitude range; (d) obtaining a first measurement from an output of the photodetector at some point in time after performing step (c); (e) after Y amount of time has elapsed since step (c) was performed and while the sensor is still in an active state, configuring the radiant source so that the radiant source does not output electromagnetic waves or configuring the radiant source so that the radiant source outputs electromagnetic waves having a frequency that is less than the lowest frequency of the certain frequency range and/or having an amplitude that is less than the lowest amplitude of the certain amplitude range; (f) configuring, after X amount of time has elapsed since step (c) was performed and while the sensor is in the active state, the radiant source so that the radiant source outputs electromagnetic waves having a frequency within the certain frequency range and having an amplitude within the certain amplitude range, wherein X is greater than zero and greater than Y; (g) obtaining a second measurement from an output of the photodetector at some point in time after performing step (f); and (h) after N amount of time has elapsed since step (f) was performed and while the sensor is in the active state, configuring the radiant source so that the radiant source does not output electromagnetic waves or configuring the radiant source so that the radiant source outputs electromagnetic waves having a frequency that is less than the lowest frequency within the certain frequency range and/or having an amplitude that is less than the lowest amplitude within the certain amplitude range, wherein N is less than X.

Advantageously, in the above method Y and N may be less than or equal to X/2. By operating the sensor according to the inventive method, the radiant source is "turned off" or dimmed for a period of time between readings of the photodetector, and, thus, the indicator molecules of the optical sensor are not continuously illuminated while the sensor is active, thereby increasing the life of the indicator molecules.

In another embodiment, the method for increasing the useful lifetime of an optical sensor that, when in an active state, obtains data regarding the presence or concentration of a substance within an area at least once every X amount of time for a continuous Z amount of time, wherein the optical sensor includes indicator molecules having an optical characteristic that is affected by the presence of the substance and a light source for exciting the indicator molecules, includes the steps of: placing the optical sensor at a location within the area; and exciting the indicator molecules for a total of not more than Y amount of time during the Z amount of time, wherein Y is less than Z.

In another aspect, the present invention provides an optical sensor having a duty cycle controller that is configured to control the duty cycle of the sensor's radiant source.

By reducing the duty cycle of the sensor's radiant source from 100% to some percent less than 100% during the periods of time when the sensor is activated, the cumulative illumination time of the indicator molecules will be reduced, thereby reducing the rate of photo-oxidation and, thus, increasing the longevity of the indicator molecules.

In another aspect, the present invention provides an optical sensor having a cooling system configured to lower the temperature of the indicator molecules. Lowering the temperature of the indicator molecules reduces the rate of photo-oxidation, and, thus, increases the useful life of the indicator molecules.

In another aspect, the present invention provides a method for determining a maximum duty cycle for a light source of an optical sensor. In one embodiment, the method includes the steps of: (a) continuously exposing indicator molecules to light emitted from a light source, which is preferably identical or substantially similar to the optical sensor's light source; (b) periodically determining the output intensity of the indicator molecules; (c) determining the amount of time it takes for the output intensity of the indicator molecules to degrade by a predetermined amount; (d) determining the total cumulative activation time for the sensor; and (e) determining the maximum duty cycle by dividing the amount of time determined in step (c) by the amount of time determined in step (d).

In yet another aspect, the present invention provides a method for determining the useful lifetime of an optical sensor. In one embodiment, the method includes the steps of: (a) continuously exposing indicator molecules to light emitted from a light source, which is preferably substantially similar or identical to a light source that will be used in the optical sensor; (b) periodically determining the output intensity of the indicator molecules; (c) determining the amount of time it takes for the output intensity of the indicator molecules to degrade by a predetermined amount; (d) determining an average expected amount of time that the light source used in the optical sensor will be on per day; and (e) determining the useful product life by dividing the amount of time determined in step (c) by the amount of time determined in step (d).

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

FIG. 10 is an illustration of certain components an optical sensor according to another embodiment of the invention.

DETAILED DESCRIPTION OF THE PREFERRED EMBODIMENT

Figure 1:
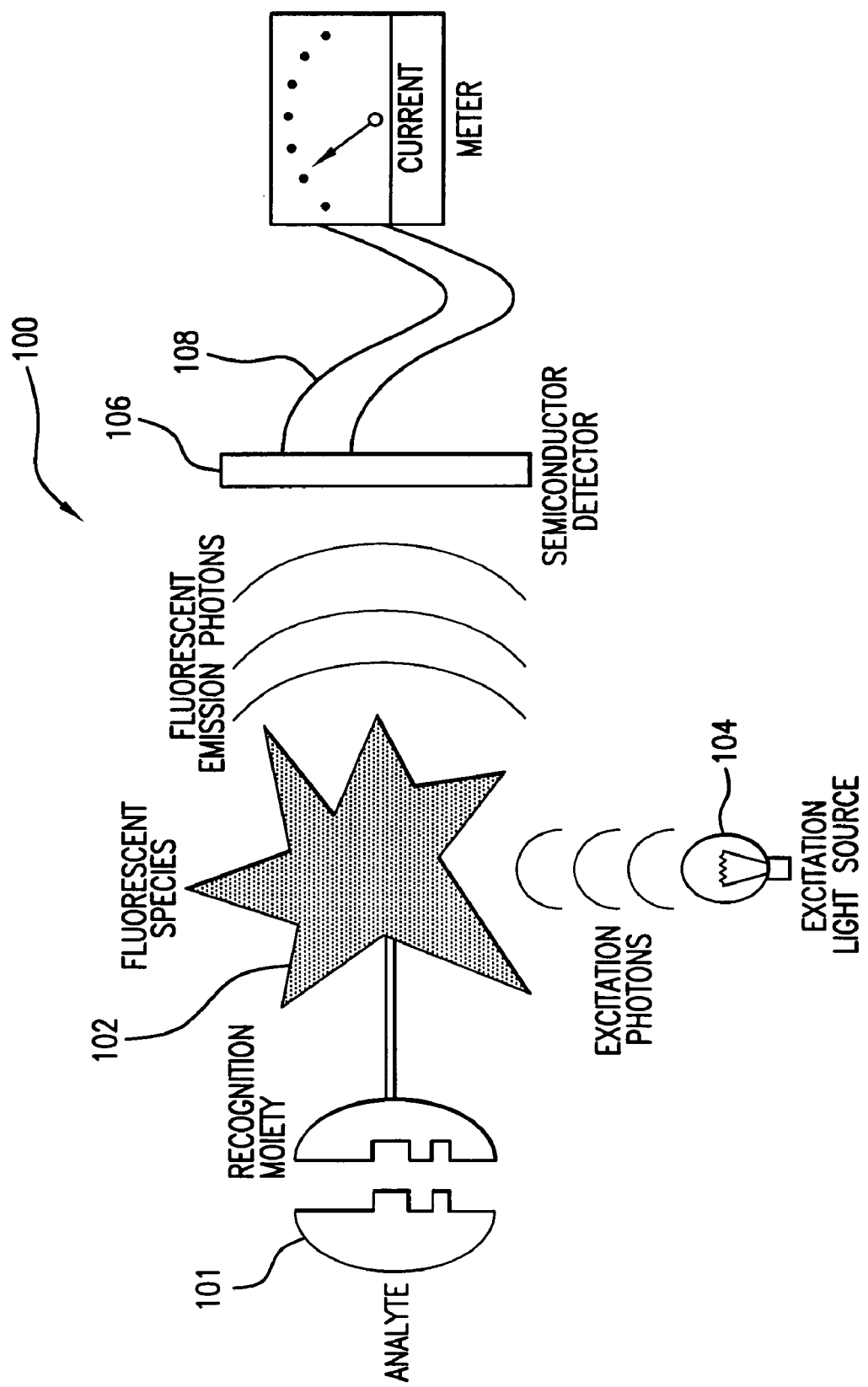
FIG. 1 is an illustration of certain components of an exemplary optical sensor.

FIG. 1 shows a schematic illustration of a representative conventional optical sensor 100 for detecting the presence or concentration of a substance 101. Sensor 100 includes indicator molecules 102, a light source 104, and a photo-electric transducer 106 (or "photodetector 106"). It can be seen from the graphic in FIG. 1 that the indicator molecules 102 are a key element in converting the presence and concentration of the substance to a measurable signal (e.g., a measurable electrical current output 108 from photodetector 106).

Figure 2:
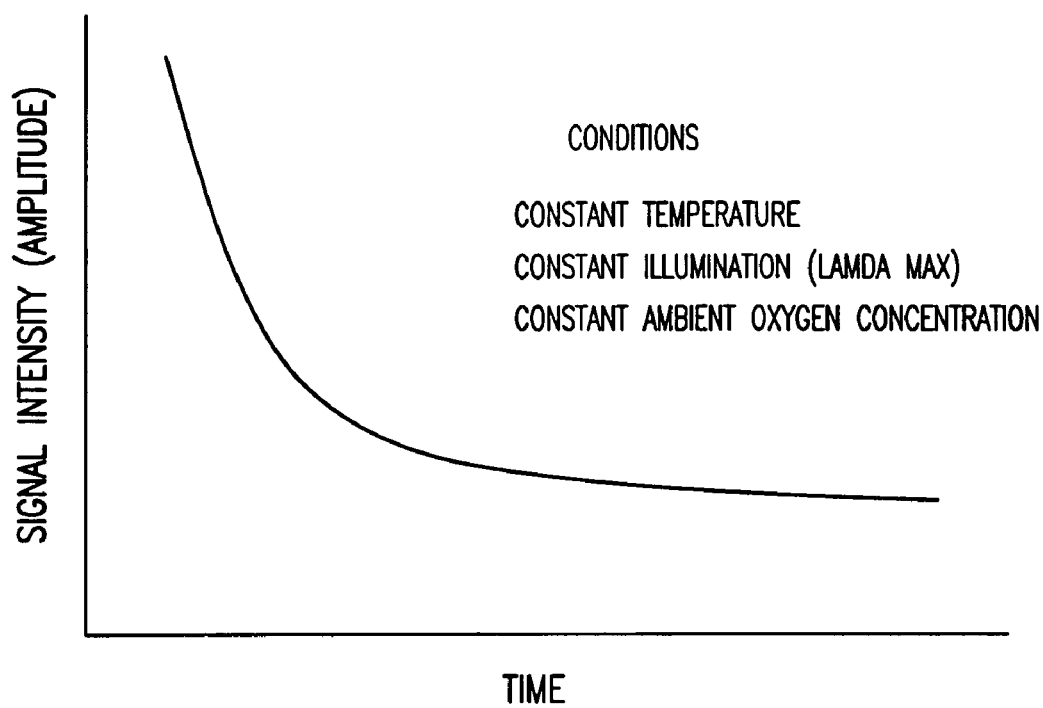
FIG. 2 is a sketch depicting a typical signal degradation plot for conventional indicator molecules under typical operating conditions.

As discussed above, photo-oxidation causes the indicator molecules to be the "weakest" component of sensor 100. That is, photo-oxidation causes the indicator molecules to degrade sooner than the other components of sensor 100. The surrounding components, such as light source 104 and photodetector 106, have useful lifetimes typically exceeding ten years. However, the indicator molecules can be degraded under typical operating conditions within hours or days. This is illustrated in FIG. 2, which is a sketch depicting a typical signal degradation plot for conventional indicator molecules under typical operating conditions (i.e., constant temperature, constant illumination, and constant ambient oxygen concentration). As shown in FIG. 2, the intensity of the radiation emitted from the indicator molecules decreases significantly over a short period of time.

Because the indicator molecules are the weakest link, the lifetime of a conventional sensor is also on the order of hours or days. The present invention, however, provides an optical sensor and method for extending the useful life of the sensor.

Figure 3:
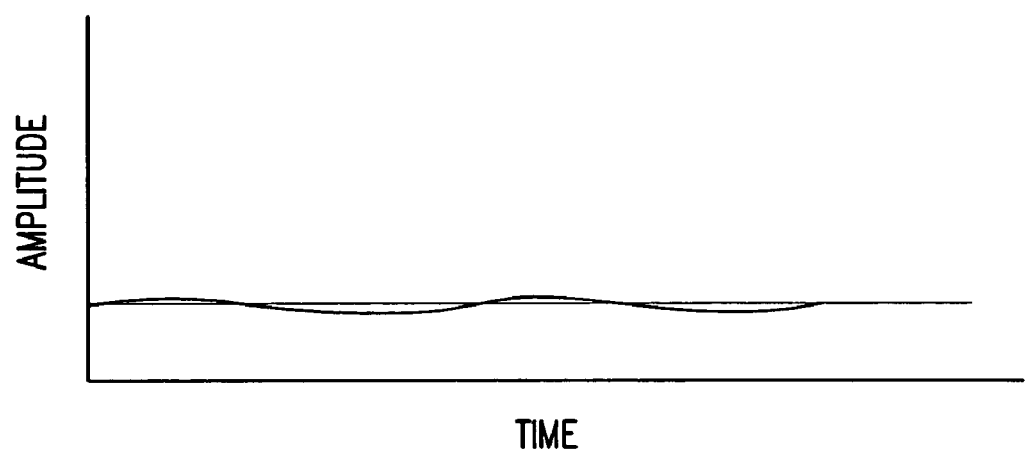
FIG. 3 is a sketch of an example background noise profile.

In a typical optical sensor (see e.g., sensor 100), the electro-optical components are conventional macro and/or micro-electronic discrete devices. These components and other non-chemical components of the sensor, along with downstream amplification circuitry, have a baseline electronic noise level intrinsic to the circuit design. There may also be some background optical noise in such a system. The noise is somewhat random, but typically remains within a relatively constant region. FIG. 3 is a sketch of an example background noise profile.

Figure 4A:
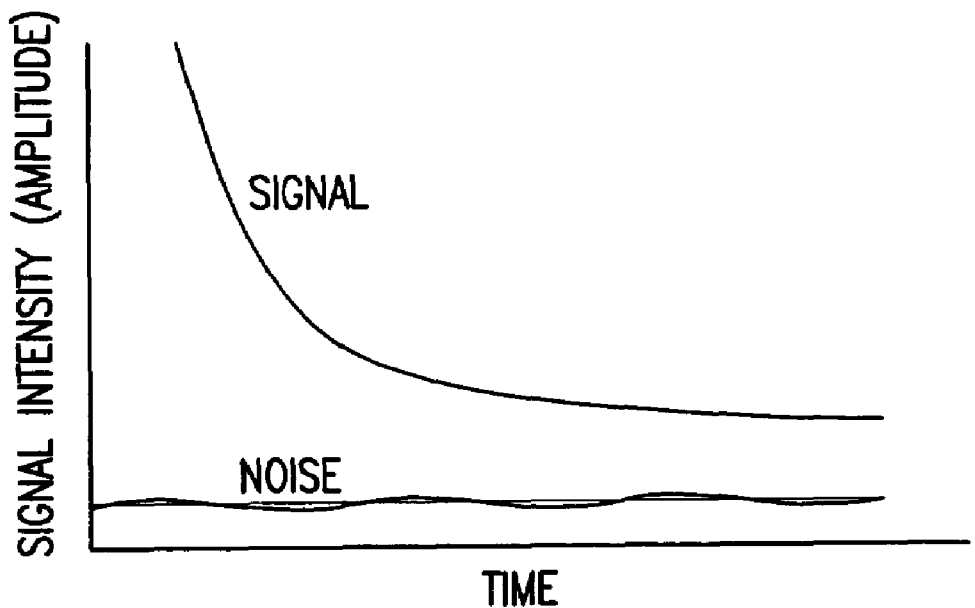
FIG. 4(A) is an overlay between FIGS. 2 and 3.

Against this constant noise backdrop, it must be possible to distinguish the signal that is directly proportional to the concentration of the substance with sufficient clarity. The ratio of an averaged signal amplitude to an average noise amplitude is known as the signal to noise ratio (SNR). The numerical value of SNR which is adequate for a given application is also dependent on other factors governing the overall design. In general, a high SNR is preferred to a low SNR. Importantly, the level of SNR that is achieved in a design establishes the precision and resolution with which a measurement can be made using the device. FIG. 4(A) is an overlay between FIGS. 2 and 3.

Figure 4B:
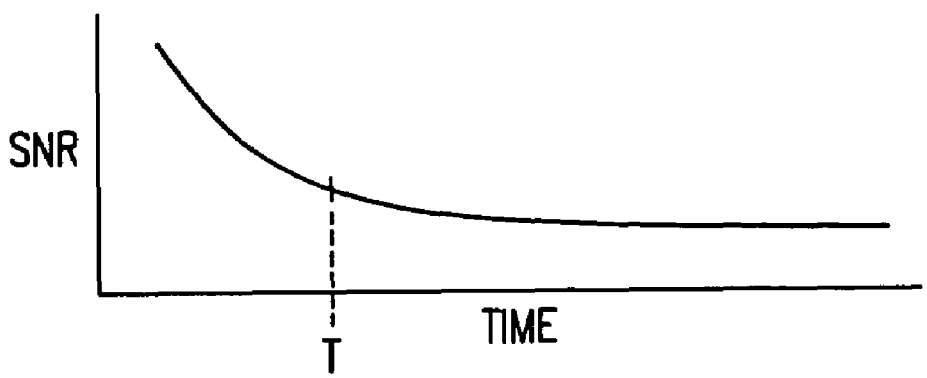
FIG. 4(B) is a plot of SNR versus time.

FIG. 4(A) shows both the relatively constant noise backdrop along with the declining signal due to photo-chemical degradation. The simple ratio of these two plots is illustrated in FIG. 4(B) as SNR versus time. As can be seen from FIG. 4(B), the SNR is eroded in direct proportion to the photo-oxidation which is destroying the signal. At some defined numerical value of SNR at time (T) along the declining SNR curve, the sensor becomes un-usable because it can no longer meet specifications for resolution and accuracy. This time (T) is the usable lifetime of the sensor, which is determined by the lifetime of the most labile component, which are the indicator molecules present within the system.

We have identified several factors that affect the degradation of the SNR of the sensor. The preferred range or settings for each factor can be used to define a preferred envelope of operation for the sensor. This envelope then establishes the operational parameters that permit extended lifetime of the device. The factors are discussed below.

Factor 1: Temperature.

Temperature is a fundamental and directly influential factor that determines the useful life of the indicator molecules, and hence the optical sensor. Because photo-oxidation is a chemical reaction like all others, the first principal model describing the influence of temperature is the Arrhenius Equation. We have found that increasing temperature increases the rate of the reaction resulting in faster degradation of the indicator molecules. The effect of increasing temperature on sensor signal degradation is shown in FIG. 5.

Figure 5:
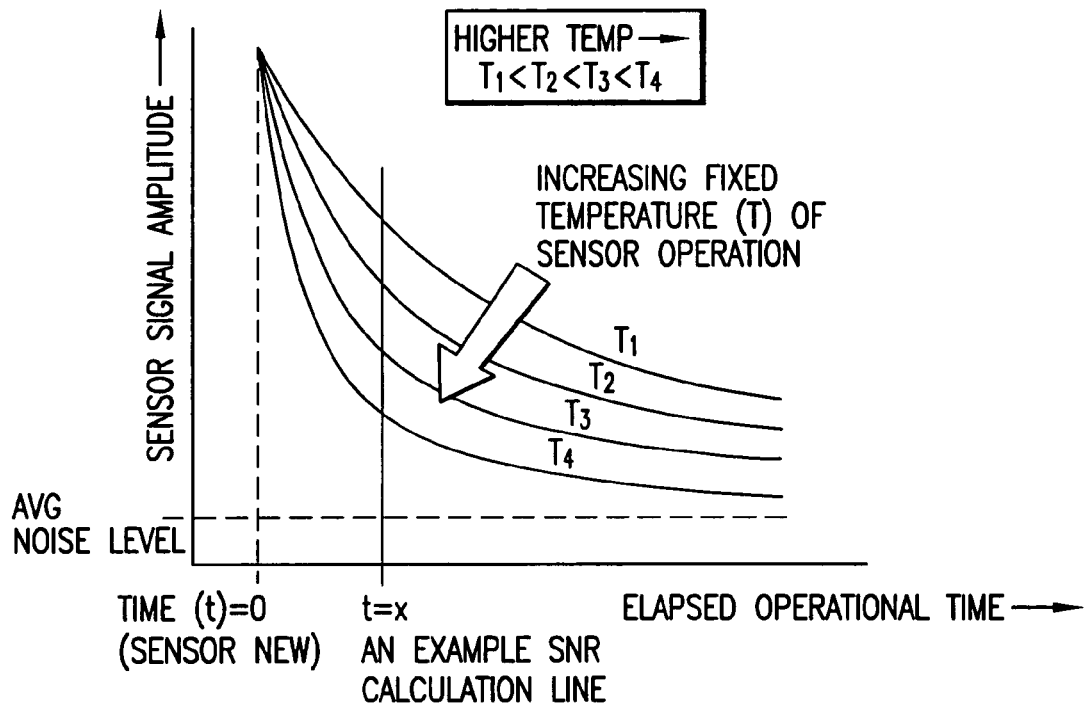
FIG. 5 illustrates the effect of increasing temperature on sensor signal degradation.
Figure 6:
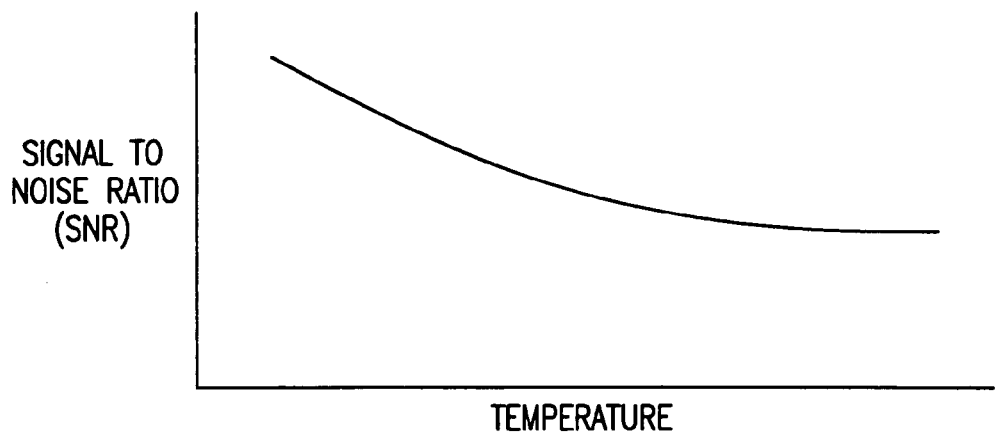
FIG. 6 is a sketch of a plot of sensor SNR versus temperature for a fixed elapsed operational time.

From FIG. 5, it can be seen that as temperature increases, the photo-chemical reaction between fluorescent species and oxygen increases, and, therefore, the signal amplitude, which is based on fluorescent intensity, decreases proportionately. FIG. 6 is a sketch of a plot of sensor SNR versus temperature for a fixed elapsed operational time.

In one aspect, therefore, the present invention provides a sensor 700 (see FIG. 7) having a cooling system 702 to maintain the temperature of the sensor, or the temperature of the indicator molecules 102, at a fixed value that provides for an optimal condition for longevity given other constraints on the design of the sensor. For example, if certain requirements dictate that sensor 700 must operate between a temperature of 50 and 70° F., then the cooling system 702 can be configured to maintain the temperature at 50° F., which, within the range of 50-70° F., is the optimal temperature with respect to longevity. For applications where there is no lower limit on the temperature of the device, we have found that the temperature could go down as low as minus 20° F.

In one embodiment, cooling system 702 may include or consist of a Peltier-type chip devices as used for cooling semiconductor components. In other embodiment, cooling system 702 may include or consist of liquid nitrogen or other coolant.

Factor 2: Separation Distance Between Light Source and Indicator Molecules.

Figure 8:
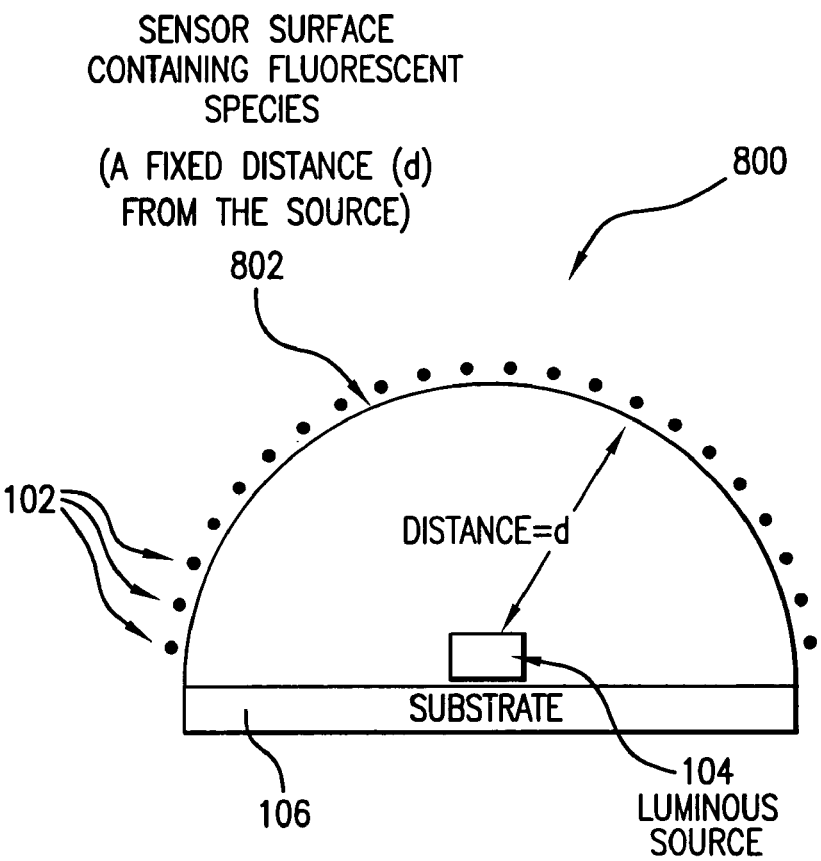
FIG. 8 is an illustration of certain components an optical sensor according to another embodiment of the invention.

In an optical sensor, such as optical sensor 800, which is depicted in FIG. 8, the luminous flux density is a luminous flux per unit area at a point on a surface. For example, if a unit of light is an Einstein (defined as 1 mole of photons, or 1 Avagardro's Number of photons), then an Einstein per unit area is a statement of flux. The density of the number of photons per unit area at the point of the indicator molecules 102 is the effective flux density for our purposes herein. Working backwards, the flux density is related to a term known as Luminous Exitance (see below) or practically, source intensity. Through the inverse square law, the photon intensity (or flux) will decrease by the square of the separation distance (d) between the light source 104 and the surface 802 where the indicator molecules 102 are installed.

Addressed as a single factor within the overall "matrix" or set of factors, we have determined that one effective, practical and preferred range of operation for the separation distance (d) is zero to 2.5 centimeters (cm). The low end of the range at zero represents a design where the indicator molecules are installed directly onto, or within, the surface of the light source 104. The far end of the range (2.5 cm) represents a design suited to a highly photo-labile fluorescent species in order to maintain the flux at lower levels. Sensors according to the present invention, however, are not limited to this specific range.

Factor 3: Luminous Exitance, Source Intensity, Power or Drive Current.

The Luminous Exitance of a light source is a measure of the flux density at the surface of the emission source (e.g., an incandescent, solid state, organic, inorganic, LED, or any light luminous source). The flux density, as described above, can be defined for any surface, real or imaginary and at any distance (d) from the source. Luminous Exitance is the flux defined at the surface of the emission source or in this case where d=0. This relates the intensity of the light source to the flux density defined at (d). Since the intensity of an electronic or electro-optical light source is also directly related to the drive current for that source, it is possible and practical to control the source intensity via the electrical drive current for the light source (it is important to note also that sources other than electronic are possible). This relationship between drive current and source intensity is a simple one and is illustrated in FIG. 9.

Figure 9:
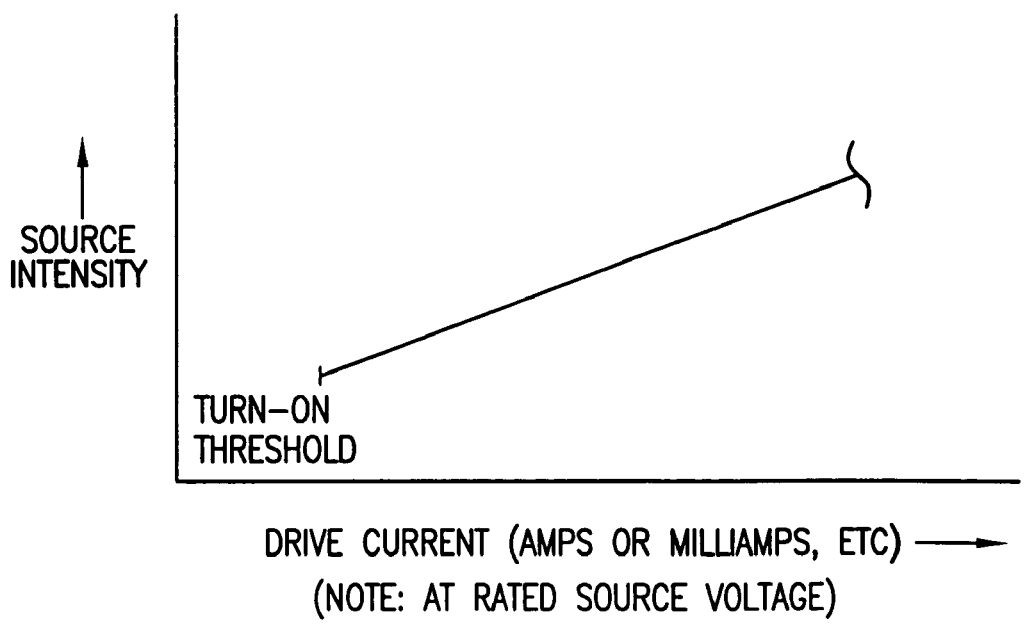
FIG. 9 is a sketch illustrating the relationship between drive current and source intensity.

The relation illustrated in FIG. 9 is also known as a de-rating curve and can be unique to a source and to the manufacturer of the source. However, this data is made available by the fabricators for a particular chosen source. It is important to note that the drive current also controls the power of the source. Luminous power is typically expressed in watts (and other units). A solid state electronic source as used in one example would typically fall within the realm of microwatts to milli-watts depending upon the current and de-rating curve. The power, within the performance limitations of the source, can be controlled and set by limiting the drive current much like a standard household dimmer switch. Although the units can become confusing, by simple conversion, power can also be directly related to photo-oxidation rate as described above.

Given the above described relationship between drive current and photo-oxidation rate at a given distance (d), the preferred drive current is the lowest possible drive current that provides a stable light source output. For typical solid-state light sources such as light emitting diodes (LEDs), this value may be as low as 0.5 mA at present. As these devices become more efficient, this threshold drive current may decrease.

Before describing further factors affecting the lifetime of an optical sensor, it is instructive to further illustrate the factors described thus far (e.g., temperature (T), separation distance (d), and drive current (Idrive)) within the context of a sensor system 1000 (see FIG. 10). The illustration in FIG. 10 ties together the concepts discussed thus far.

Figure 7:
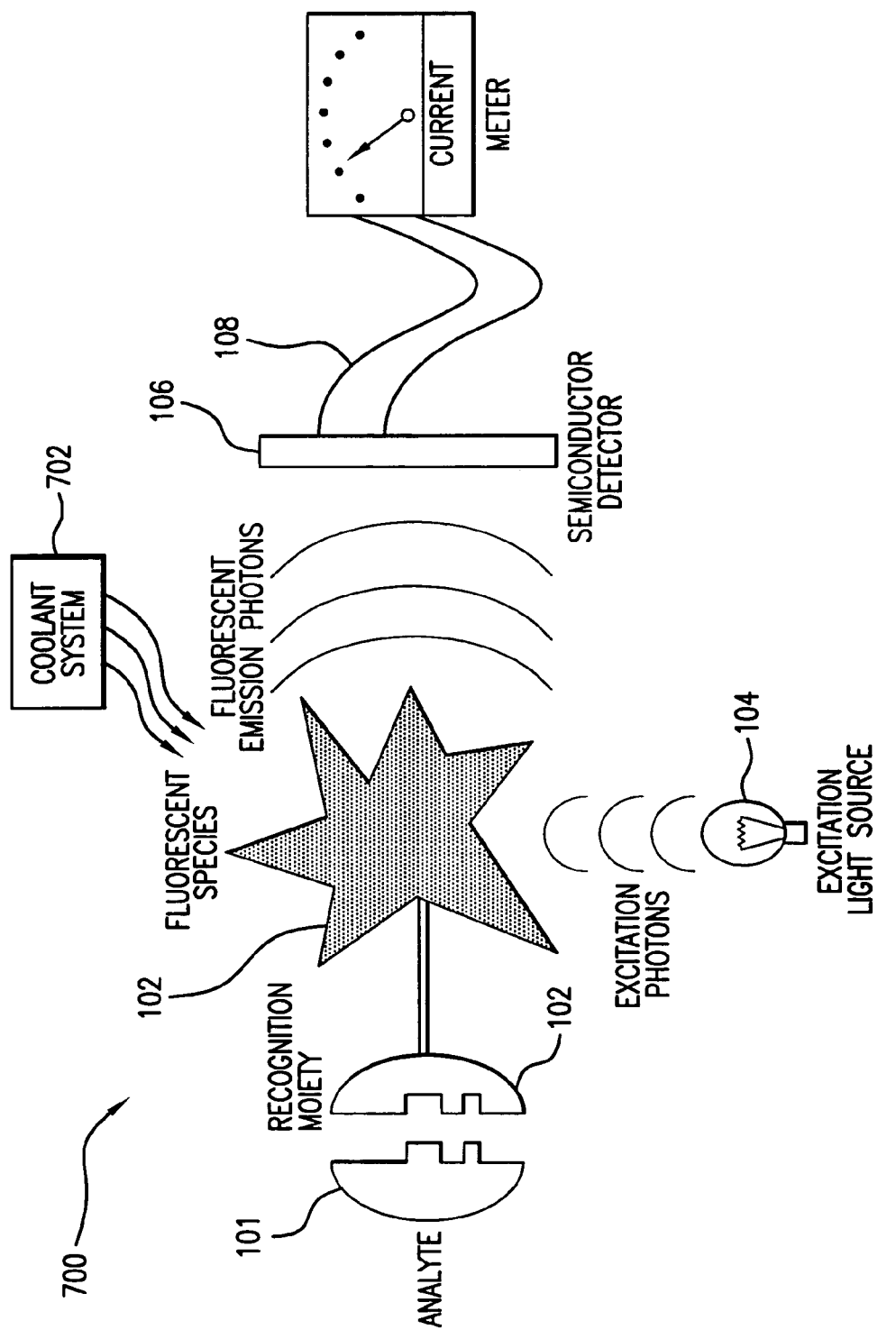
FIG. 7 is an illustration of certain components of an optical sensor according to one embodiment of the invention.

FIG. 10 illustrates a sensor system 1000 having a light source 104 enclosed or partially enclosed by a surface 802 onto or into which are placed indicator molecules 102. Sensor system 1000 further includes a power supply 1012 (e.g., a battery or other power source) for powering the light source 104 and a current controller 1014 that is used to adjust the drive current (Idrive) provided to the light source 104. Sensor 1000 may also include cooling system 702 (as illustrated in FIG. 7). An operator or a processing device can configure current controller 1014 and, thereby, set the amount of drive current.

As discussed above, the drive current sets the light source intensity, the source intensity sets the flux density through a distance (d) and the inverse square law, and the flux density is directly proportional to the rate of photo-oxidation of the indicator molecules. Therefore, the regulation of the drive current provided to light source 104 sets the source intensity, which through a fixed distance (d), governed by the inverse square law, establishes the flux, which sets the rate of photo-oxidation and thus the rate of signal degradation.

Figure 11:
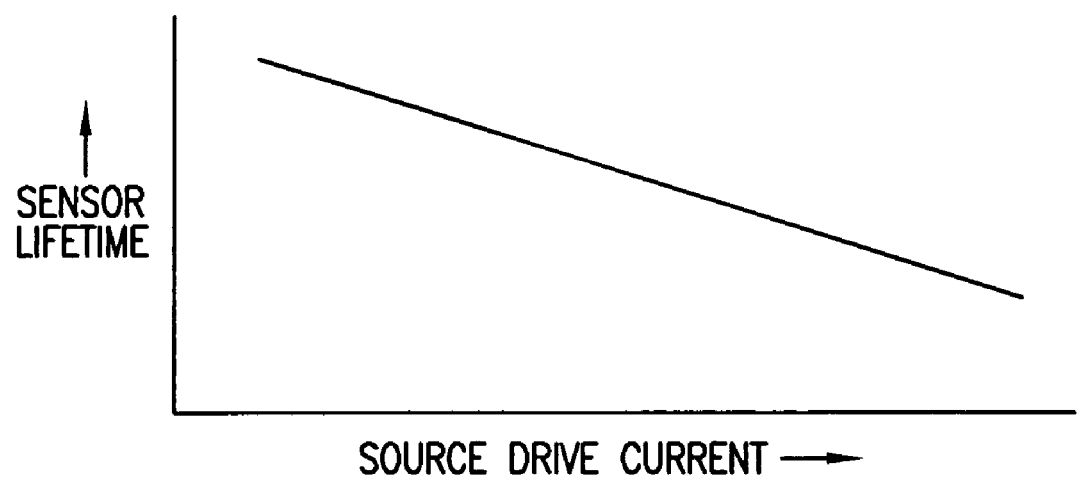
FIG. 11 is a sketch of a plot of optical sensor lifetime versus source drive current where the separation distance (d) and the temperature (T) of the system are held constant.

FIG. 11 is a sketch of a plot of sensor system 1000 lifetime versus source drive current where the separation distance (d) and the temperature (T) of the system are held constant. FIG. 11 provides a simplified but clear understanding of one of the factors in achieving extended longevity for an optical sensor.

In many cases, "d" is fixed by design. That is, the application of the optical sensor determines the acceptable range of d, which, in some cases, may be a small range. For example, if the optical sensor is to be used in vivo, then the appropriate size of the sensor and, hence, d is limited. Once d is fixed, it is possible to use this value to evaluate the other factors discussed herein (e.g., drive current) to provide additional design and optimal operational parameters.

A constant d establishes the flux at the fluorescent species surface. Note that flux and power at the surface defined by d are synonyms. As discussed above, we determined one preferred range at which d should be fixed to be between zero and 2.5 cm. Using this information to set the drive current, we determined that the current for a representative LED source to range from the threshold value (FIG. 9), which is the lowest current which will activate the source, to a value nearly twice the manufacturer's rated current flow for a solid state source. For a typical SiC or GaN based LED as an example, these drive currents range from approximately 0.5 milliamps to approximately 40 milliamps. In other embodiments, the drive currents are preferably approximately 0.8 to approximately 3 milliamps and most preferably approximately 1 to 2 milliamps. In the future, as source manufacturers build more efficient sources, these ranges can change.

Two additional factors that affect the lifetime of a sensor employing indicator molecules are (1) input luminous source energy, and (2) duty cycle. Each will be discussed in turn below.

Factor 4: Input Luminous Source Energy (or Wavelength).

The energy of a photon is related to its frequency by the equation: $E=hf$, where "E" is the energy of the photon, "h" is "Planck's Constant" and "f" is frequency. Frequency is inversely proportional to wavelength. Therefore, shorter wavelength photons have a higher energy than longer wavelength photons. Typical fluorescence excitation occurs at wavelengths from approximately 200 nm to almost 500 nm (although molecules and mechanisms are known for excitation wavelengths up through near infrared). Fluorescent absorption and emission spectra are essentially energy plots whereby the spectra is roughly a Gaussian distribution about an optimal absorption or emission peak wavelength corresponding to energy maxima within the particular molecular structure of the fluorescent species. For most fluorescent species that could be used in a sensor, the optimal wavelength (or in some cases wavelengths), will be determined by the indicator molecule itself. Thus, a designer or user of a sensor has limited freedom selecting the wavelength(s) of the light source(s).

Factor 5: Duty Cycle of the Light Source.

Unlike the wavelength of the light source, the duty cycle of the light source, which is another energy component in the design of optical sensors and which is different (but related to) the photon energy described above, is variable and under the control of the sensor designer/user. The duty cycle of the light source is the percentage of time that the source is functioning to illuminate the indicator molecules as needed to get a reading from the indicator molecules. Above some minimum duty cycle, the performance of an optical sensor with respect to the needed data output is not influenced greatly, or at all, by changes in the duty cycle. Thus, a designer/user of an optical sensor has a great deal of freedom in selecting the duty cycle of the light source without fear of adversely affecting the performance of the optical sensor. As discussed below, lowering the duty cycle of the light source can greatly increase the effective longevity of the indicator molecules, and hence the longevity of the sensor.

In an optical sensor, the total and cumulative radiant energy outputted by the light source drives the overall extent of photo-oxidation of the indicator molecules. In other words, when there is no light, there is no photo-oxidation. The cumulative power (or flux at the surface) over time is energy. A typical unit of radiant energy is Joules where: Energy (Joules)=watts (power)×seconds.

Note that Power (Energy/Time), which is the rate in which energy is consumed in lighting the light source, is directly linked to the rate of photo-oxidation of the indicator molecules. Accordingly, a higher power source photo-bleaches an indicator molecule more rapidly than a lower power source. As can be seen from the equation above, one way to control power is to control the rate at which energy is input into the system. In the case of an optical sensor, one way to control the power is to control the duty cycle of the light source.

We have discovered that in an optical sensor it is generally unnecessary for the light source to be operating or "on" during the entire period of time when the optical sensor is "active" (e.g., consuming power). In many applications, the optical sensor need be active only for a short period of time a few times per day. For example, in one embodiment, the optical sensor is active for approximately 7 minutes and for approximately 5 times per day. However, in some embodiments, the optical sensor needs to be active 24 hours each day (i.e., continuously active).

For example, if a reading from the photodetector 106 is required once every second during the period of time when the optical sensor is active, then it is not required that the light source be on during the entire period of time when the optical sensor is active. Instead, depending on the sensor circuitry, it may be sufficient to turn on the light source for only 1/10 of a second every second. In this scenario, the cumulative energy input to the system over the lifetime of the sensor would be reduced by 10 fold. Similarly, if the light source were powered for only 1/100 of a second every second, then the energy input to the system would be reduced 100 fold. Since power is directly related to cumulative photo-oxidation, and thus degradation of signal amplitude, and thus degradation of SNR, reducing the energy input by 100 fold will increase the longevity of the device by 100 fold for this single factor.

The appropriate duty cycle of the light source during the period of time when the sensor is active is application specific. In one application, when the sensor is active, a reading from the photodetector 106 is made approximately every 2-minutes. The sensor and supporting electronic circuitry (e.g., photodetector 106) is sufficiently fast to permit an accurate reading to be taken within a period of 100 milliseconds or 1/10 of a second. Powering the sensor light source for 1/10 of a second out of every two minute interval provides an energy reduction factor of 120 seconds/0.1 seconds=1200×. This factor translates directly into a 1200-fold extended product lifetime for the sensor versus continuous operation against photo-oxidative signal degradation of the fluorescent species.

Duty cycles are often expressed as a percent of on-time. The example above would thus be an approximately 0.08% duty cycle. For different products, different designs, and different indicator molecules, duty cycles of approximately 50% and potentially higher are useful. On the low end, fractional percentages to very low levels are useful even as low as 1×10(exp-5)%.

In other embodiments of the present invention, the sensor is turned on approximately every 2 minutes for approximately 50 milliseconds of LED on-time. This embodiment may be useful for a glucose sensor.

Figure 12:
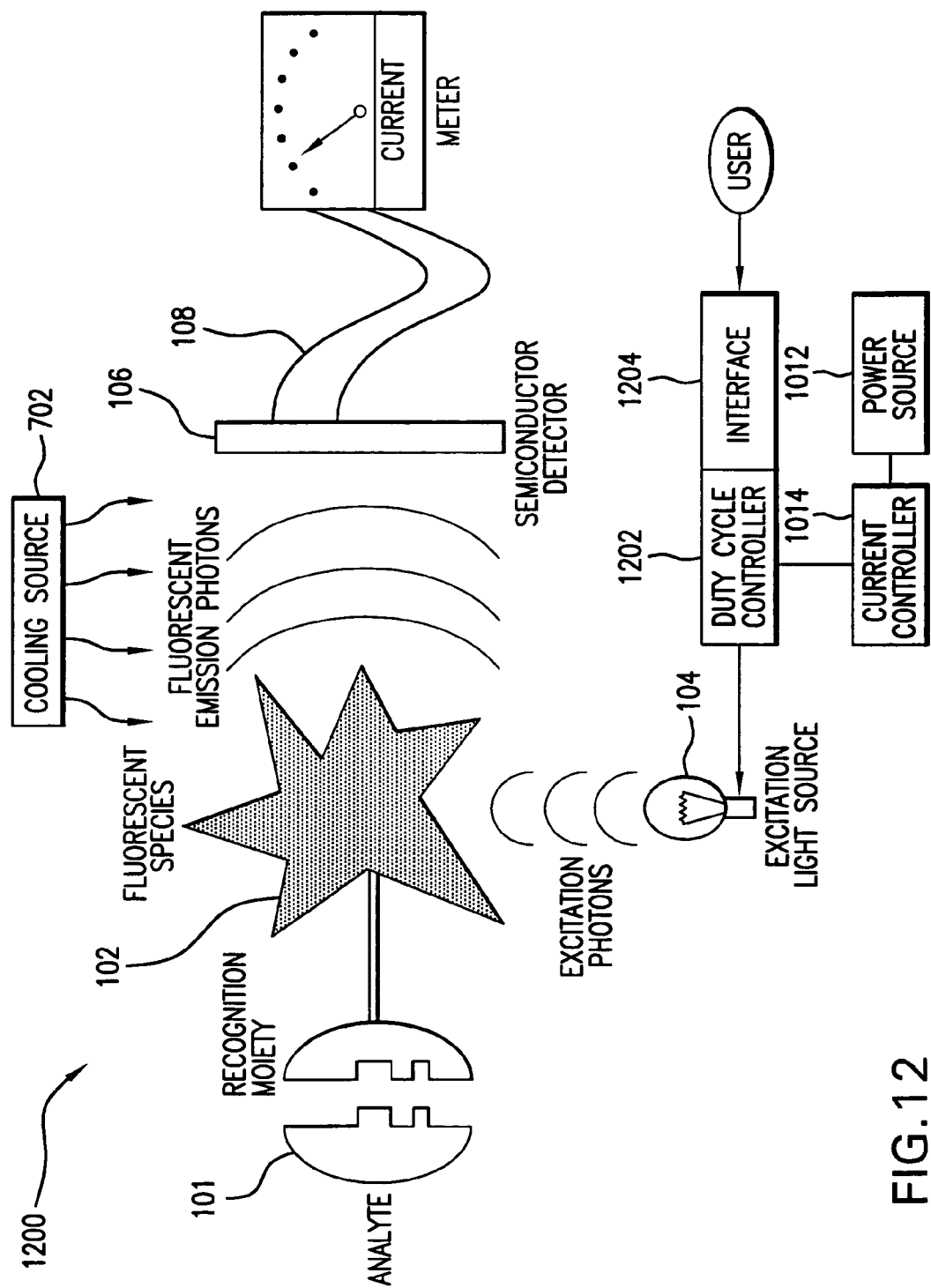
FIG. 12 illustrates certain components of an optical sensor according to another embodiment of the invention.

FIG. 12 illustrates an optical sensor 1200 according to another embodiment of the invention. Sensor 1200 is identical to sensor 700, with the exception that sensor 1200 further includes a duty cycle controller 1202 and a current controller 1014. The components of sensor 1200 are preferably enclosed within a housing (not shown). The indicator molecules may be placed on the surface of the housing or in the surface of the housing.

Figure 17:
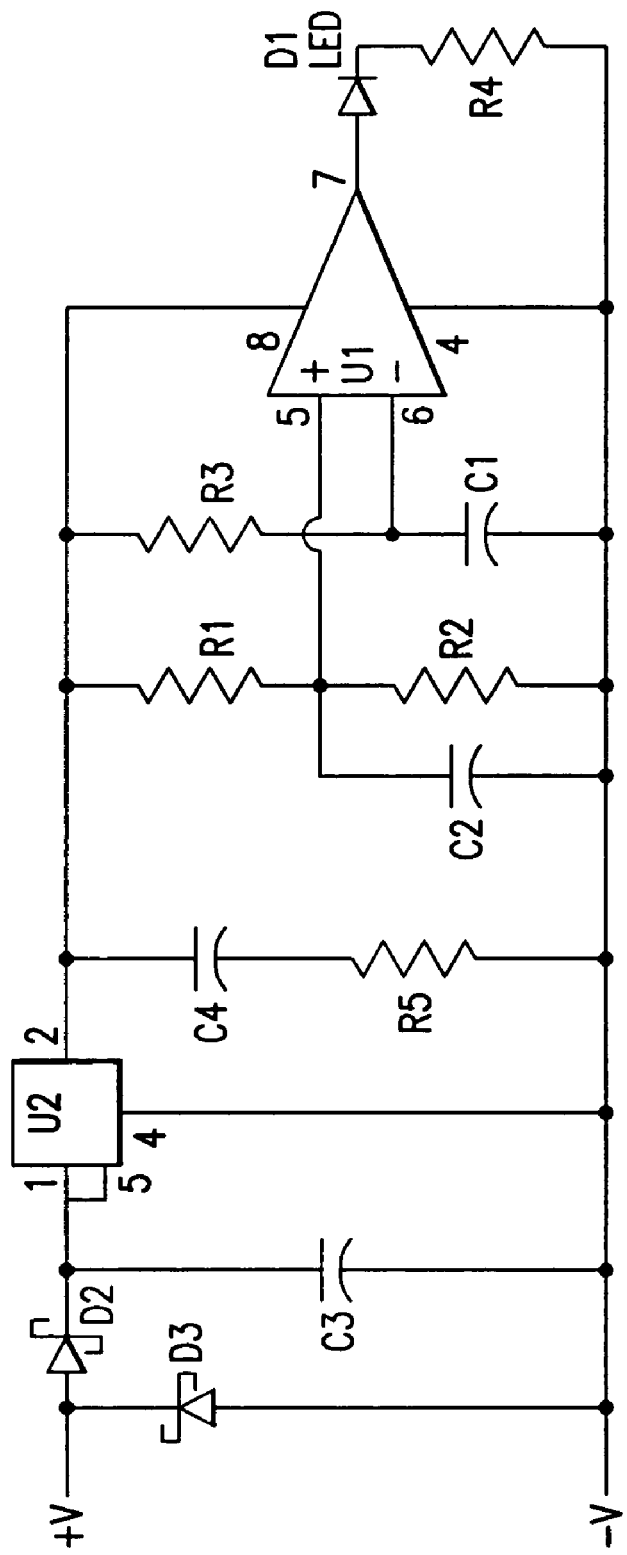
FIG. 17 is a circuit diagram illustrating an example circuit that may be used to control the light source of the sensor.

Duty cycle controller 1202 can be implemented solely in hardware or in a combination of hardware and software. Duty cycle controller 1202 controls the duty cycle of light source 104. In some embodiments, a user of sensor 1200 can set the duty cycle of light source 104 by configuring duty cycle controller 1202. In these embodiments, duty cycle controller 1202 has an interface 1204 that enables the user to configure or set the controller. FIG. 17 is a circuit diagram illustrating an example circuit that may be used to control the operation of light source 104.

Figure 13:
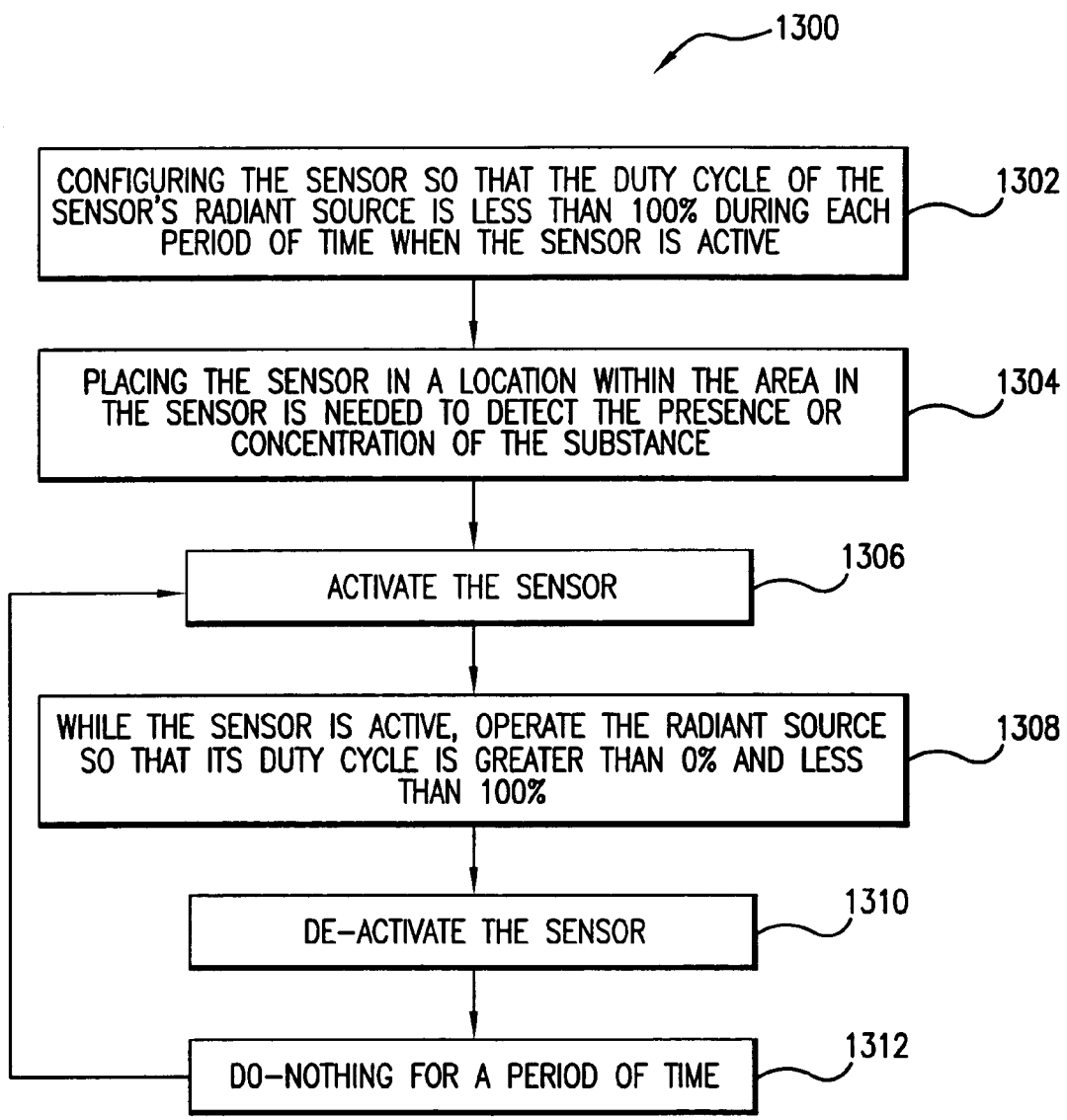
FIG. 13 is a flow chart illustrating a process according to one embodiment of the invention.

FIG. 13 is a flow chart illustrating a process 1300, according to one embodiment of the invention. Process 1300 is a process for increasing the lifetime of an optical sensor (e.g., sensor 1200) that, when active, is configured to obtain data regarding the presence or concentration of a substance within an area at least once every X unit of time for a continuous Z amount of time. X and Z can be anywhere from seconds to minutes to hours.

Process 1300 may begin in step 1302, where the optical sensor is configured so that the duty cycle of the sensor's radiant source is less than 100% during the Z amount of time when the sensor is required to obtain the data at least once every X unit of time. In step 1304, the sensor is placed in a location within the area. Step 1304 may be performed before or after step 1302. In some applications of the optical sensor, X is about 1 second and Z is about 7 minutes. In other applications, X may be more or less than 1 second and Z may be more or less than 7 minutes. Also, in some applications the duty cycle for the Z amount of time is less than 50%, but in other applications the duty cycle may go as low as 0.00001% or lower. In step 1306, the sensor is activated and remains in the active state for Z amount of time. The sensor may be activated by providing power to the sensor from an external power source.

In step 1308, during the Z amount of time when the sensor is active, the radiant source is turned on and then off a number of times. That is, it is operated so that the duty cycle of the radiant source is greater than 0% but less than 100%. In some particular embodiments, the duty cycle is less than 50%. In step 1310, after z amount of time has elapsed from when step 1306 was performed, the sensor is de-activated. Next, the sensor may do nothing for a period of time (step 1312). After step 1312, the process may return to step 1306.

Figure 14:
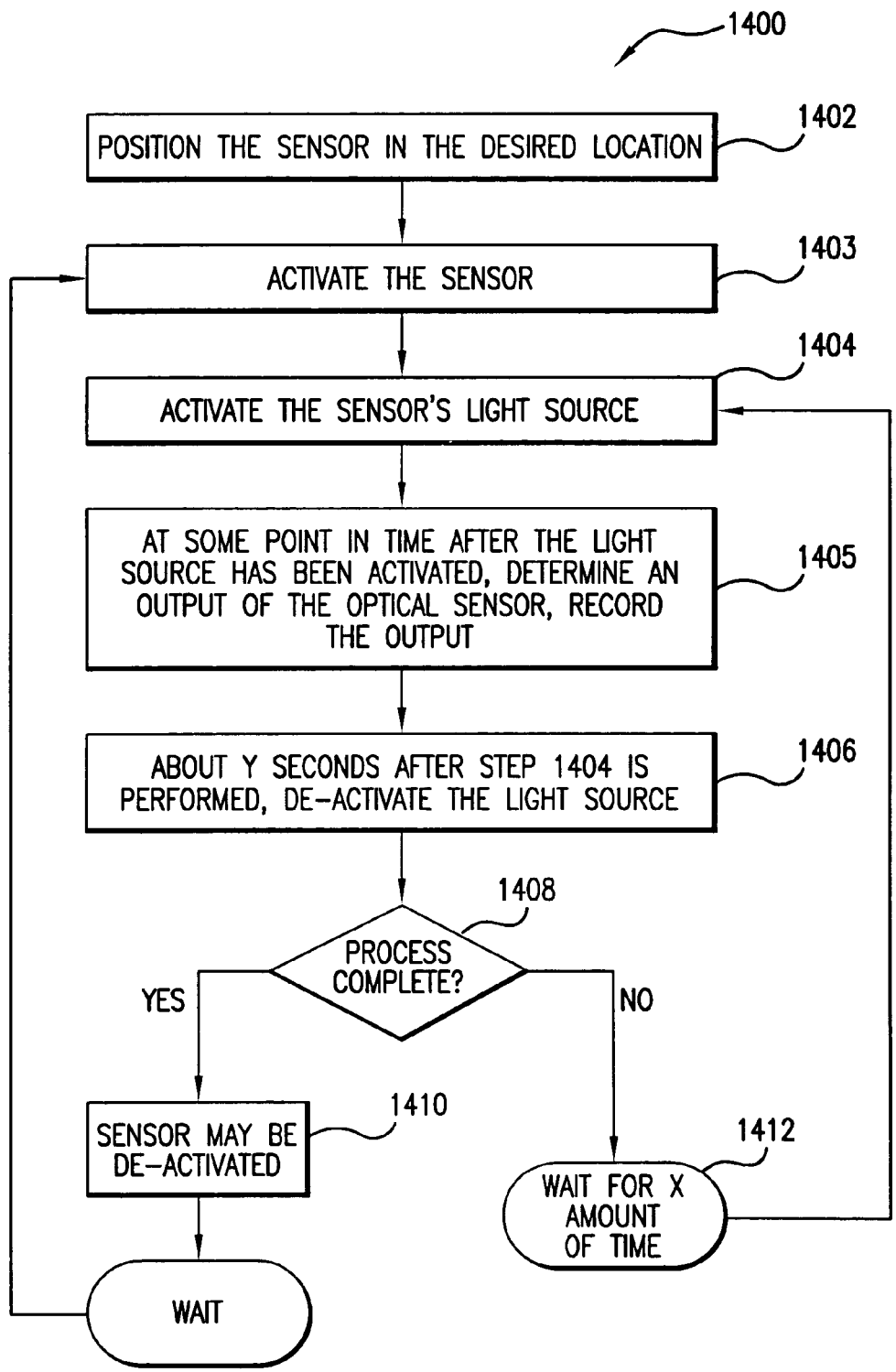
FIG. 14 is a flow chart illustrating a process according to another embodiment of the invention.

FIG. 14 is a flow chart illustrating a process 1400, according to another embodiment of the invention, for sensing the presence or concentration of a substance in a particular area. Process 1400 may begin in step 1402, where an optical sensor is positioned in the desired location within the area (e.g., implanted in vivo, for example). In step 1403, the sensor is activated. For example, the sensor may be activated by providing power to the sensor from an external power source.

In step 1404, after the sensor is activated, the light source of the sensor is turned on (e.g., the light source is configured to have a minimum luminous exitance). In step 1405, at some point in time after the light source has been turned on, an output of the photodetector 106 is determined and, preferably, recorded. In step 1406, which is performed about Y amount of time after step 1404 is performed, the light source is turned off.

In step 1408, a determination is made as to whether process 1400 is complete. For example, process 1400 may be complete when Z amount of time has elapsed since step 1404 was first performed. If the process is complete, then the sensor is de-activated (step 1410). After the sensor is de-activated, the sensor may be re-activated at a later time. For example, in some embodiments, the sensor is required to be activated 5 times each day for a year. Thus, in these embodiments the sensor is re-activated about 5 hours after being de-activated.

If the process is not complete, then the process returns to step 1404, but only after about X amount of time has elapsed since step 1404 was last performed (step 1412).

Steps 1404-1406 are typically repeated for about a given period of time Z (that is, the sensor is active for about Z amount of time before being de-activated). In process 1400, X is greater than zero (0), Y is preferably less than X, and X is less than Z. In some application, Y is less than or equal to X/2. In other applications Y may be less than or equal to X/10.

Figure 15:
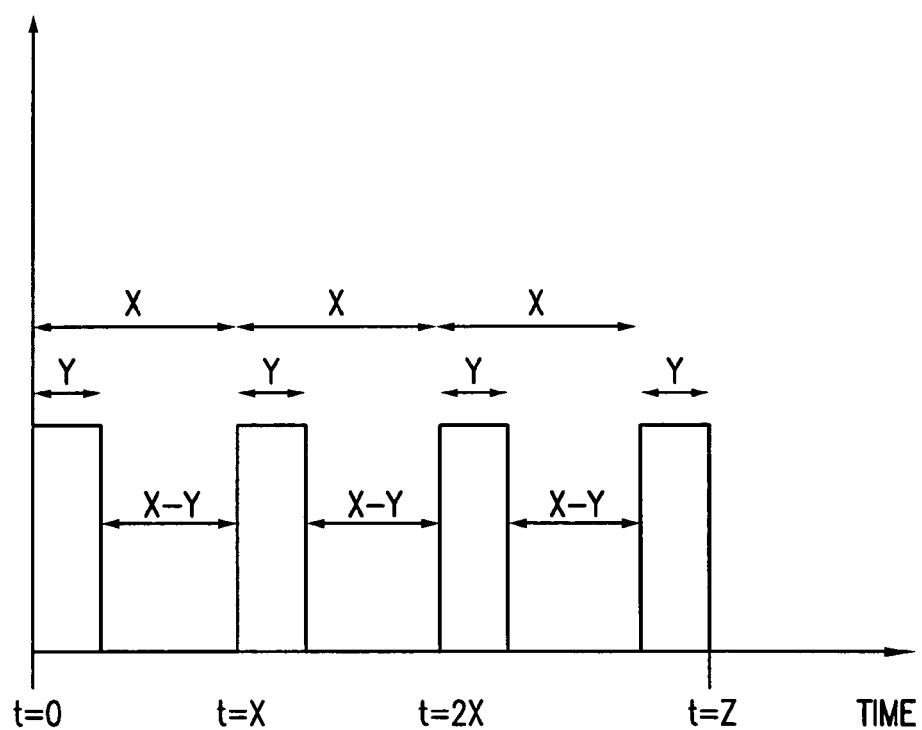
FIG. 15 is a sketch illustrating an exemplary duty cycle of an optical sensor light source operated according to an embodiment of the invention.

The configuration of the radiant source over the Z period of time (i.e., the time period when the sensor is active) is illustrated in FIG. 15. As shown in FIG. 15, at t=0, t=X, t=2X, etc. the light source is activated for Y amount of time and then de-activated for X-Y amount of time. Although FIG. 15 illustrates a periodic function, the function need not be periodic nor is Y or X required to remain constant over the Z period.

By performing process 1400, the useful lifetime of the optical sensor's indicator molecules can be increased because the light source is not continuously "on" while the optical sensor is active.

Figure 16:
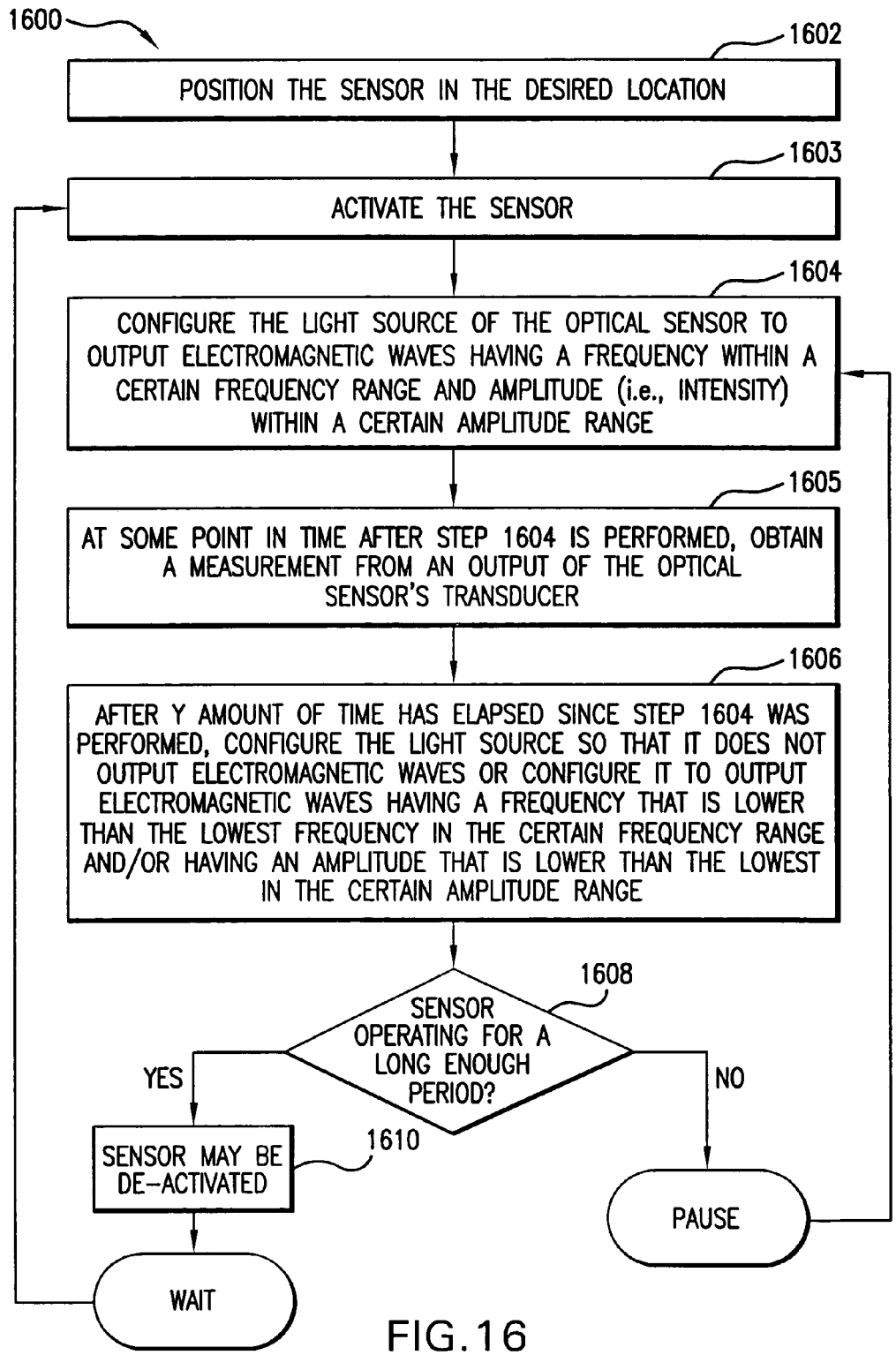
FIG. 16 is a flow chart illustrating a process according to another embodiment of the invention.

FIG. 16 is a flow chart illustrating a process 1600, according to another embodiment of the invention, for sensing the presence or concentration of a substance. Process 1600 may begin in step 1602, where an optical sensor is positioned in the desired location. In step 1603, the sensor is activated.

In step 1604, the light source of the optical sensor is configured to output electromagnetic waves having a frequency within a certain frequency range and amplitude (i.e., intensity) within a certain amplitude range. In step 1605, a measurement from an output of the optical sensor's photodetector is obtained at some point in time after step 1604 is performed, and, preferably, before step 1606 is performed.

In step 1606, which is performed after Y amount of time has elapsed since step 1604 was performed, the light source is configured so that it does not output electromagnetic waves or the source is configured to output electromagnetic waves having a frequency that is not within the certain frequency range and/or having an amplitude that is lower than the lowest amplitude in the certain amplitude range. Preferably, the amplitude of the wave, if any, emitted in step 1606, is less than the lowest amplitude within the certain amplitude range.

In step 1608, a determination is made as to whether the sensor has been operating for a sufficiently long enough period. If it has, the sensor is may be de-activated (step 1610), but if it has not, then the process returns to step 1604 after a delay of X amount of time measured from the performance of step 1606. After step 1610, the process may return to step 1603 after a certain amount of time has elapsed.

Like process 1400, process 1600 can greatly increase the lifetime of the optical sensor's indicator molecules, especially in the case where in step 1606 the source is configured to not output any electromagnetic waves or to output such waves having a relatively small amplitude and/or low frequency.

FIG. 17 is a circuit diagram illustrating an example of a circuit that may be used to control the light source of the sensor. In this non-limiting example, resisters R1 and R2 are a voltage divider, with filter capacitor C2, that together supply a reference voltage to comparator U1 input pin 5. When power is first applied to the circuit, capacitor C1 is discharged. With comparator U1 positive input pin 5 higher than negative input pin 6, output pin 7 supplies voltage to light LED D1 through current limit resistor R4. Capacitor C1 charges toward the applied power voltage through resistor R3. When C1 voltage passes the reference voltage, U1 negative input pin 6 becomes higher than positive input pin 5. U1 output pin 7 then falls to −v, turning off LED D1.

Other reference voltages also could be used. For example, a commercial voltage reference integrated circuit or a Zener diode could be used. Also, other devices, such as an op amp, could be used instead of the comparator circuit illustrated in FIG. 17.

In addition to the processes described above related to the operation of an optical sensor, the present invention also provides a process for determining a desired duty cycle of the light source and a process for determining the useful product life of an optical sensor.

Figure 18:
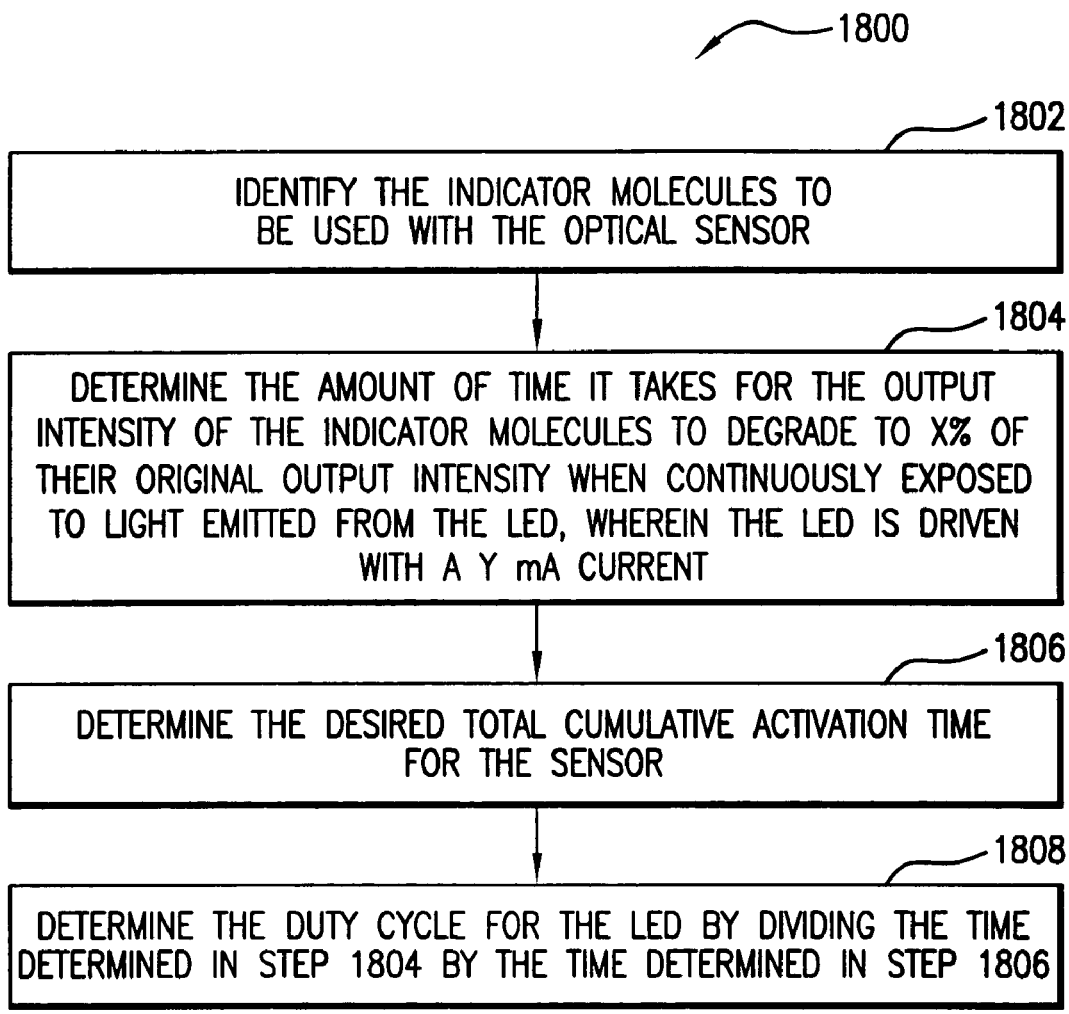
FIG. 18 is a flow chart illustrating a process for determining a duty cycle.

FIG. 18 is a flow chart illustrating a process 1800 for determining a desired duty cycle for the LED of an optical sensor, wherein the LED is driven with a Y mA current. Process 1800 may begin in step 1802, where the indicator molecules to be used with the optical sensor are identified. In step 1804, the amount of time it takes for the output intensity of the indicator molecules to degrade to X % of their original output intensity when continuously exposed to light emitted from the LED being driven with a Y mA current is determined, where Y mA is the drive current that will be used when the optical sensor is activated.

In step 1806, the total cumulative activation time for the sensor is determined. For example, if the sensor is designed to be activated for 7 minutes 5 times every day for 365 days, then the total cumulative activation time of the sensor is (7×5×365=12775 minutes). In step 1808, the duty cycle for the LED is determined by dividing the time determined in step 1804 by the time determined in step 1806. Accordingly, the duty cycle is the percentage of time the LED is on during the period of time when the sensor is active.

Figure 19:
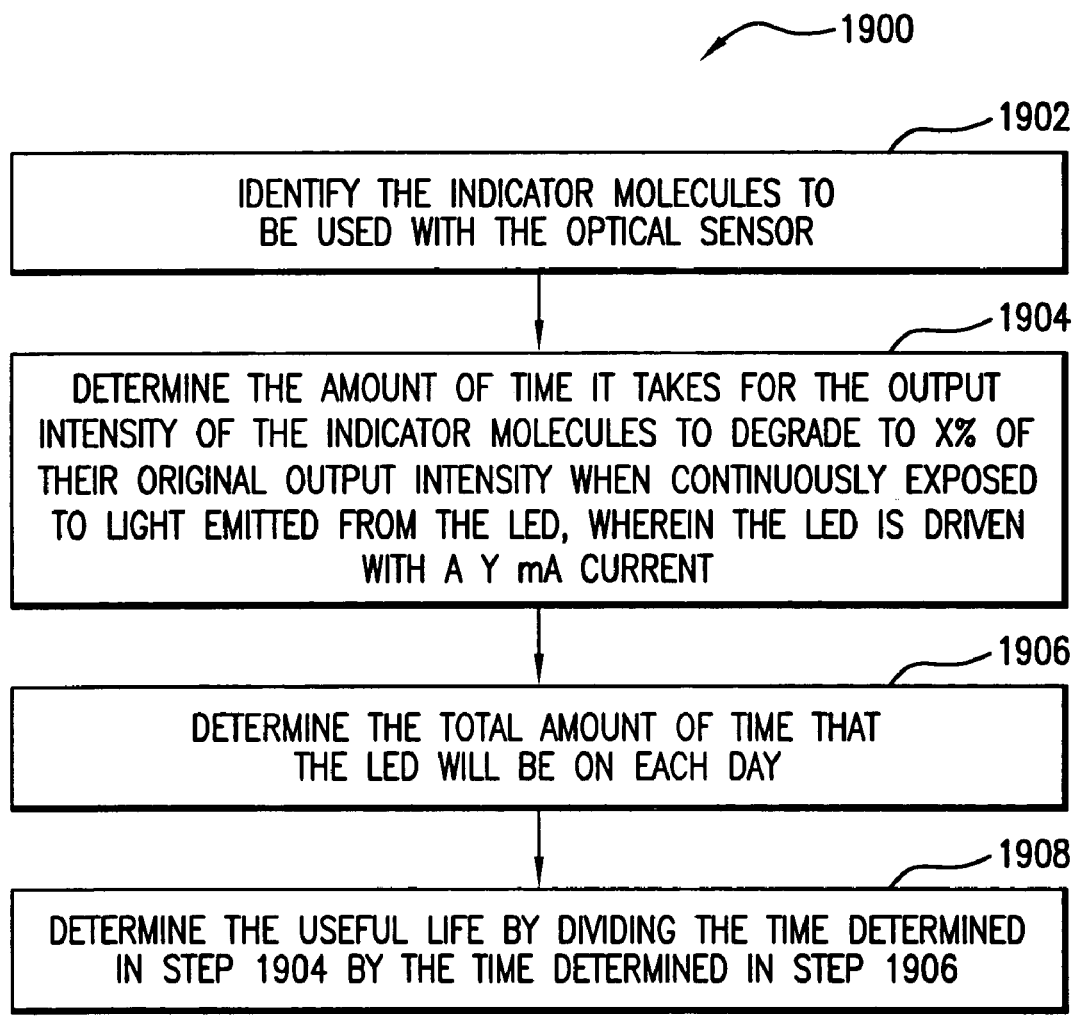
FIG. 19 is a flow chart illustrating a process for determining the useful product lifetime of an optical sensor.

FIG. 19 is a flow chart illustrating a process 1900 for determining the useful product lifetime of an optical sensor, wherein the sensor has an LED that when turned on is driven with a Y mA current, the LED is turned on for the same amount of time each day, and the useful product life is defined as the amount of time it takes for the output intensity of the indicator molecules of the sensor to degrade to X % of their original output intensity.

Process 1900 may begin in step 1902, where the indicator molecules to be used with the optical sensor are identified. In step 1904, the amount of time it takes for the output intensity of the indicator molecules to degrade to X % of their original output intensity when continuously exposed to light emitted from the LED being driven with a Y mA current is determined, where Y mA is the drive current that will be used when the optical sensor is activated.

In step 1906, the total amount of time that the LED will be on each day is determined. In step 1908, the useful product life is determined by dividing the amount of time determined in step 1904 by the amount of time determined in step 1906. For example, if the amount of time determined in step 1904 is 10000 minutes and the LED will be on for not more than 10 minutes each day, then the useful product life of the sensor will be approximately 10000/10=1000 days.

A non-limiting example of a process for determining a desired duty cycle for an optical sensor is described as follows. In accordance with this example, it is desired that the optical sensor be used 5 times per day, with each use being 7 minutes long, over 365 days (1 year). During each use, the LED is on for a total of 150 ms per sample, with a sample occurring once every second during use. The LED is driven by a square wave and therefore has a duty cycle of 50%. This application requires that the sensor stay within 10% of its original output intensity over the course of a year under conditions as compared to its initial output intensity.

The amount of LED on-time can be calculated for this example as follows.

1) In one year, there are (365 days per year)*(5 uses per day)=1,825 uses per year.
2) Each sample occurs at 1 second intervals, so there are 60 samples per minute.
3) There are (60 samples per minute)*(7 minutes per use)=420 samples per use.
4) Using equations 1 and 3 above, the sensor is used for (420 samples per use)*(1,825 uses per year)=766,500 samples per year.
5) For each sample, the sensor's LED is on for 150 ms.
6) From equations 4 and 5, one obtains the sensor's LED on-time of (766,500 samples per year)*(150 ms per sample)=114,975,000 ms per year.
7) From equation 6, one may convert 114,975,000 ms per year=114,975 seconds per year=31.94 hours LED on-time per year, at 50% duty-cycle.

Thus, the requirements of this application are that the LED be able to run for approximately 31.94 hours continuously, at 50% duty-cycle, and still have the output intensity of the sensor remain within 10% of its original value.

In this example, the sensor output intensity vs. LED operating time at 1 mA reveals that the sensor output intensity will degrade to 90% of its original value in 23 hours of continuous use, at 50% duty-cycle. Because this is not enough LED on-time for this specific application, the duty-cycle can be changed to compensate. For example, changing the duty cycle to 25% (or half of its value) will half the LED on-time and thus decrease the amount of photo-bleaching of the indicator. The sensor's lifetime will, in this specific example, be close to double its original lifetime.

The 50% duty-cycle comes from the use of a square-wave that drives the LED. For each cycle of the wave, the LED drive signal is on for a certain duration, "t" seconds, then switches off for the same duration "t" seconds, then switches on for "t", and so forth, alternating between on and off. Half of the time it is on and half of the time it is off. This can be changed, for example, to be on for a $\frac{1}{4}^{th}$ of the cycle, and off for $\frac{3}{4}^{ths}$ of the cycle. In this case, the LED on-time will be halved for the same usage requirements and thus can be run longer and still stay within the 10% degradation limit.

If any of the times listed in this example are decreased, it will decrease the total on-time of the LED and thus extend the lifetime of the sensor by preserving the intensity of the indicator molecules. For example, decreasing the number of days per year the device is used, decreasing the number of uses per day, decreasing the number of samples per use, decreasing the length of time the LED is on during a sample, and decreasing the duty-cycle of the LED drive will extend the lifetime of the sensor. A simple formula can be used to obtain the total LED on-time per year:

Total LED on-time per year=(number of days per year the device is used)*(number of uses per day)*(number of samples per use)*(length of time the LED is on during a sample)*(duty-cycle of the LED drive)

The optical sensors described herein are not limited to any particular application or operating environment. For example, sensors according to the present invention may be implanted into a person and used to measure various biological analytes in the human body (e.g., glucose, oxygen, toxins, etc).

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for increasing the lifetime of an optical sensor that, when active, is configured to obtain data regarding the presence or concentration of a substance within an area, wherein the optical sensor includes (i) indicator molecules having an optical characteristic that is affected by the presence of the substance and (ii) a radiant source, the method comprising:

(a) utilizing the optical sensor configured so that the duty cycle of the radiant source is greater than 0% but less than 100% during the period of time when the optical sensor is active;

(b) positioning the optical sensor at a location within the area;

(c) activating the optical sensor for a period of Z amount of time after performing step (b), wherein Z is greater than 0;

(d) operating the radiant source so that the duty cycle of the radiant source is greater than 0% but less than 100% during said Z amount of time when the optical sensor is active; and (e) de-activating the optical sensor after said Z amount of time has elapsed, wherein Z is determined prior to activating the optical sensor.

2. The method of claim 1, wherein the duty cycle is less than or equal to about 50%.

3. The method of claim 1, wherein the duty cycle is less than or equal to about 10%.

4. The method of claim 1, wherein the duty cycle is less than or equal to about 1%.

5. The method of claim 1, wherein the duty cycle is less than or equal to about .1%.

6. The method of claim 1, wherein Z is about .5 to about 20 minutes.

7. The method of claim 1, wherein Z is about 1 to about 10 minutes.

8. The method of claim 1, wherein Z is about 7 minutes.

9. The method of claim 1, wherein Z is about 2 minutes.

10. The method of claim 1, wherein the optical sensor is activated for approximately 200 milliseconds every approximately 2 minutes.

11. The method of claim 10, wherein the radiant source is activated for approximately 100 milliseconds of the approximately 200 milliseconds the optical sensor is activated.

12. The method of claim 1, wherein the indicator molecules are fluorescent.

13. The method of claim 1, wherein the radiant source comprises a light emitting diode (LED).

14. The method of claim 1, wherein the drive current used to drive the LED is about less than or equal to 3 mA.

15. The method of claim 14, wherein the drive current used to drive the LED is about less than or equal to 2 mA.

16. The method of claim 14, wherein the drive current used to drive the LED is about less than or equal to 1 mA.

17. The method of claim 1, wherein the sensor further includes a cooling element.

18. The method of claim 1, wherein the indicator molecules are absorbance-type indicator molecules.

19. The method of claim 1, further comprising:

(f) determining whether a first predetermined amount of time has elapsed since de-activating the optical sensor after said Z amount of time has elapsed;

(g) activating the optical sensor in response to determining that the first predetermined amount of time has elapsed since de-activating the optical sensor after said Z amount of time has elapsed;

(h) after performing step (g), determining whether a second predetermined amount of time has elapsed since performing step (g); and (i) de-activating the optical sensor in response to determining that the second predetermined amount of time has elapsed since performing step (g).

20. A method for increasing the useful lifetime of an optical sensor that provides data regarding the presence or concentration of a substance within an area, wherein the optical sensor includes (i) indicator molecules having an optical characteristic that is affected by the presence of the substance, (ii) a radiant source and (iii) a photodetector, the method comprising:

(a) positioning the sensor in a location in the area;

(b) activating the sensor, thereby placing the sensor in an active state;

(c) after performing step (b), utilizing the radiant source configured so that the radiant source outputs electromagnetic waves having a frequency within a certain frequency range and having an amplitude within a certain amplitude range;

(d) obtaining a first measurement from an output of said photodetector at some point in time after performing step (c);

(e) after Y amount of time has elapsed since step (c) was performed and while the sensor is still in an active state, utilizing the radiant source configured so that the radiant source does not output electromagnetic waves or utilizing the radiant source configured so that the radiant source outputs electromagnetic waves having a frequency that is less than the lowest frequency of said certain frequency range and/or having an amplitude that is less than the lowest amplitude of said certain amplitude range;

(f) utilizing, after X amount of time has elapsed since step (c) was performed and while the sensor is in the active state, the radiant source configured so that the radiant source outputs electromagnetic waves having a frequency within said certain frequency range and having an amplitude within said certain amplitude range, wherein X is greater than zero and greater than Y;

(g) obtaining a second measurement from an output of said photodetector at some point in time after performing step (f);

(h) after N amount of time has elapsed since step (f) was performed and while the sensor is in the active state, utilizing the radiant source configured so that the radiant source does not output electromagnetic waves or utilizing the radiant source configured so that the radiant source outputs electromagnetic waves having a frequency that is less than the lowest frequency within said certain frequency range and/or having an amplitude that is less than the lowest amplitude within said certain amplitude range, wherein N is less than X; and (i) deactivating the sensor after Z amount of time has elapsed, where Z is greater than X.

21. The method of claim 20, wherein X is less than about 5 minutes.

22. The method of claim 20, wherein Y is less than X/2.

23. The method of claim 20, wherein Y is less than or equal to X/10.

24. The method of claim 20, wherein Y is less than one second.

25. The method of claim 20, wherein the indicator molecules are fluorescent.

26. The method of claim 20, wherein the radiant source comprises a light emitting diode (LED).

27. The method of claim 26, wherein step (b) includes the step of driving the LED with a drive current, wherein the drive current is about equal to the LED's threshold drive current.

28. The method of claim 20, wherein the step of activating the sensor comprises the step of providing power to electrical components of the sensor.

29. The method of claim 20, wherein Y and N are both about 150 milliseconds and X is about 1 second.

30. An optical sensor, comprising:
   indicator molecules having an optical characteristic that is affected by the presence of a substance;
   a light source;
   a duty cycle controller configured to repeatedly turn on the light source for an amount of time and then turn it off for an amount of time while the optical sensor is being utilized to sense the presence or concentration of the substance; and
   an interface, coupled to the duty cycle controller, to enable a user to configure the duty cycle controller.

31. The optical sensor of claim 30, further comprising a photodetector that receives light emitted from the indicator molecules.

32. The optical sensor of claim 30, wherein, while the optical sensor is being utilized to sense the presence or concentration of the substance, the duty cycle controller is configured to turn the light source on for not more than Y amount of time every X amount of time, where X is greater than Y.

33. The optical sensor of claim 32, wherein Y is less than or equal to about X/2.

34. The optical sensor of claim 32, wherein Y is about 150 milliseconds and X is about 1 second.

35. The optical sensor of claim 32, wherein Y is about 100 milliseconds and X is about 1 second.

36. The optical sensor of claim 32, wherein Y is about 50 milliseconds and X is about 1 second.

37. An optical sensor, comprising:
   indicator molecules having an optical characteristic that is affected by the presence of a substance;
   a light source;
   control means for repeatedly turning on the light source for an amount of time and then turning it off for an amount of time while the optical sensor is being utilized to sense the presence or concentration of the substance; and
   an interface, coupled to the control means, to enable a user to configure the control means.

38. The optical sensor of claim 37, further comprising a photodetector that receives light emitted from the indicator molecules.

39. The optical sensor of claim 38, wherein, while the optical sensor is being utilized to sense the presence or concentration of the substance, the control means turns the light source on for not more than Y seconds every X seconds, where X is greater than Y.

40. The optical sensor of claim 39, wherein Y is less than or equal to about X/2.

41. The optical sensor of claim 39, wherein Y is about 150 milliseconds and X is about 1 second.

42. An optical sensor, comprising:
   indicator molecules having an optical characteristic that is affected by the presence of a substance;
   a light source that, when turned on, illuminates the indicator molecules;
   a photoelectric transducer that receives light emitted from the indicator molecules; and
   a cooling element configured to reduce the temperature of the indicator molecules.

43. The optical sensor of claim 42, further comprising a duty cycle controller for repeatedly turning on the light source for an amount of time and turning off the light source for an amount of time while the optical sensor is being utilized to sense the presence or concentration of the substance.

44. The optical sensor of claim 43, wherein, while the optical sensor is being utilized to sense the presence or concentration of the substance, the duty cycle controller turns the light source on for not more than Y seconds every X seconds, where X is greater than Y.

45. The optical sensor of claim 44, wherein Y is less than or equal to about X/2.

46. A method for increasing the useful lifetime of an optical sensor, wherein the optical sensor includes indicator molecules having an optical characteristic that is affected by the presence of the substance and a light source for exciting the indicator molecules, the method comprising:
   placing the optical sensor at a location within the area;
   activating the optical sensor;
   after activating the optical sensor and at at least three distinct points in time within a first time period of a predetermined Z amount of time, exciting the indicator molecules for not more than a predetermined Y amount of time, wherein Y is less than Z and each of the three points in time is separated from each of the other two points in time by more than Y amount of time;
   in response to said Z amount of time having elapsed, operating the optical sensor so that the indicator molecules are not excited for at least W amount of time, wherein W is greater than 2Z; and
   after said W amount of time has elapsed and at at least three distinct points in time within a second time period of Z amount of time, exciting the indicator molecules for not more than Y amount of time, wherein Y is less than Z and each of the three points in time is separated from each of the other two points in time by more than Y amount of time.

47. The method of claim 46, wherein Y is less than Z/3.

48. The method of claim 46, wherein Y is less than Z/10.

49. The method of claim 46, wherein Y is less than Z/100.

50. The method of claim 46, wherein the step of placing the optical sensor at a location within the area comprises implanting the optical sensor in a human being.

51. The method of claim 50, wherein the substance is a biological analyte.

52. The method of claim 51, wherein the biological analyte is glucose.

53. The method of claim 46, wherein Z is less than about 10 minutes.

54. The method of claim 53, wherein Y is less than about 1 second.

55. A method for determining the useful lifetime of an optical sensor, comprising:
   (a) continuously exposing indicator molecules to light emitted from a light source;
   (b) periodically determining the output intensity of the indicator molecules;
   (c) determining the amount of time it takes for the output intensity of the indicator molecules to degrade by a predetermined amount;

(d) determining an average expected amount of time that the optical sensor's light source will be on per unit time; and (e) determining the useful product life by dividing the amount of time determined in step (c) by the amount of time determined in step (d).

56. The method of claim 55, further comprising providing to a user information representing the useful product life that was determined in step (e).

57. A method for determining a maximum duty cycle for a light source of an optical sensor, comprising:

(a) continuously exposing indicator molecules to light emitted from a light source;

(b) periodically determining the output intensity of the indicator molecules;

(c) determining the amount of time it takes for the output intensity of the indicator molecules to degrade by a predetermined amount;

(d) determining the total cumulative activation time for the sensor; and (e) determining the maximum duty cycle by dividing the amount of time determined in step (c) by the amount of time determined in step (d).

58. The method of claim 57, further comprising providing to a user information representing the maximum duty cycle that was determined in step (e).

* * * * *